(12) United States Patent
Pauletti et al.

(10) Patent No.: US 6,326,148 B1
(45) Date of Patent: Dec. 4, 2001

(54) DETECTION OF COPY NUMBER CHANGES IN COLON CANCER

(75) Inventors: Giovanni E. Pauletti, Santa Monica; Dennis J. Slamon, Woodland Hills, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/351,763

(22) Filed: Jul. 12, 1999

(51) Int. Cl.$^7$ ........................................................ C12Q 1/68
(52) U.S. Cl. ........................................................ 435/6
(58) Field of Search ........................................... 435/6

(56) References Cited

U.S. PATENT DOCUMENTS 5,892,010 * 4/1999 Gray et al. .......................... 536/23.1

FOREIGN PATENT DOCUMENTS

WO98/02539    1/1998    (WO) .

OTHER PUBLICATIONS

Ried et al "Comparative Genomic Hybridization Reveals a specific pattern of chromosomal gains and losses during the genesis of colorectal tumors" Genes, Chromosomes, and Cancer, vol. 15, p. 235–245, 1996.*

Collins et al "Positional cloning of ZNF217 and NABC1: Genes amplified at 20q13.2 and overexpressed in breast carcinoma" Proc. Natl. Acad. vol. 95, p. 8703–8708, Jul. 1998.*

Wang et at "Cot–1 Banding of Human choromosomes using FISH hybridization with CY3 labeling" Jpn. J. Hum. Genetics, vol. 40, p. 243–252, 1995.*

Korn et al "Chromosome arm 20q gains and other genomic alterations in colorectal cancer metastic to liver, as analyzed by CGH and FISH" Genes, Chromosomes, and Cancer, vol. 25, p. 82–90, Jun. 1999.*

Brown et al "Exploring the new world of the genome with DNA microarrays" Nature Genetics Supplement, vol. 21, p. 33–37, Jan. 1999.*

Schlegel et al "Comparative Genomic in Situ hybridization of Colon carcinomas with Replication error" Cancer Research, vol. 55, p. 6002–6005, Dec. 1995.*

Nanashima et al "Gain of Chromosome 20 is a frequent aberration in liver metastasis of colorectal cancers" Digestive Disease and Sciences, vol. 42, No. 7, p. 1388–1393, Jul. 1997.*

Korn et al "Characterization of copy number increases of chromosome 20q sequences in hepatic of colorectal cancer by FISH" Proc. of the Am. Association for Cancer Research, vol. 39, p. 346, Mar. 1998.*

Bischoff et al "A homologue of Drosophila aurora kinase is oncogenic and amplified in human colorectal cancers" The EMBO Journal, vol. 17, No. 11, p. 3052–3065, Jun. 17, 1998.*

Savelieva et al "20q gain associates with immortalization: 20q13.2 amplification correlates with genome instability in human papillomavirus 16 E7 transformed human uroepithelial cells" Oncogene, vol. 14, No. 5, p. 551–560, Feb. 1997.*

Nakao et al "Genetic Changes in Primary colorectal cancer by CGH" Jpn. J. Surg. vol. 28, No. 5, p. 567–569, 1998.*

Meijer et al "Progression from colorectal adenoma to carcinoma is associated with non–random chromosomal gains as detected by CGH" J. Clinical Pathology, vol. 51, p. 901–909, Dec. 1998.*

Baker et al., "p53 gene mutations occur in combination with 17p allelic deletions as late events in colorectal tumorigenesis," *Cancer Research* (1990) 50: 7717–22.

Fearon and Vogelstein, "A genetic model for colorectal tumorigenesis," *Cell* (1990) 61: 759–767.

Vogelstein et al., "Genetic alterations during colorectal –tumor development," *New England Journal of Medicine* (1988) 319: 525.

* cited by examiner

*Primary Examiner*—Lisa B. Arthur
*Assistant Examiner*—Jeanine Goldberg
(74) *Attorney, Agent, or Firm*—Townsend and Townsend and Crew LLP

(57) ABSTRACT

The present invention provides methods of screening for colon carcinoma cells in a sample. The methods comprise providing a nucleic acid sample from a premalignant lesion in colorectal tissue from a human patient and contacting the sample with a nucleic acid probe that selectively hybridizes to a chromosomal region at 20q.

25 Claims, No Drawings

DETECTION OF COPY NUMBER CHANGES IN COLON CANCER

FIELD OF THE INVENTION

This invention pertains to the field of cancer genetics and cytogenetics. In particular, this invention pertains to the identification of an association between amplification of regions on chromosome 20 and colorectal cancer.

BACKGROUND OF THE INVENTION

Chromosome abnormalities are often associated with genetic disorders, degenerative diseases, and cancer. The deletion or multiplication of copies of whole chromosomes and the deletion or amplifications of chromosomal segments or specific regions are common occurrences in cancer (Smith (1991) *Breast Cancer Res. Treat*. 18: Suppl. 1:5–14; van de Vijer (1991) *Biochim. Biophys. Acta*. 1072:33–50). In fact, amplifications and deletions of DNA sequences can be the cause of a cancer. For example, proto-oncogenes and tumor-suppressor genes, respectively, are frequently characteristic of tumorigenesis (Dutrillaux (1990) *Cancer Genet. Cytogenet*. 49: 203–217). Clearly, the identification and cloning of specific genomic regions associated with cancer is crucial both to the study of tumorigenesis and in developing better means of diagnosis and prognosis.

One of the amplified regions found in studies of breast cancer cells is on chromosome 20, specifically, 20q13.2 (see, e.g. WO98/02539). Amplification of 20q13.2 was subsequently found to occur in a variety of tumor types and to be associated with aggressive tumor behavior. Increased 20q13.2 copy number has been found in 40% of breast cancer cell lines and 18% of primary breast tumors (Kalliioniemi (1994) *Proc. Natl. Acad. Sci. USA* 91: 2156–2160). Copy number gains at 20q13.2 have also been reported in greater than 25% of cancers of the ovary (Iwabuchi (1995) *Cancer Res*. 55:6172–6180), colon (Schlegel (1995) *Cancer Res*. 55: 6002–6005), head-and-neck (Bockmuhl (1996) *Laryngor*. 75: 408–414), brain (Mohapatra (1995) *Genes Chromosomes Cancer* 13: 86–93), and pancreas (Solinas-Toldo (1996) *Genes Chromosomes Cancer* 20:399–407).

A number of studies have elucidated genetic alterations that occur during the development of colorectal tumors. For instance, deletions of p53 genes on chromosome 17p are often late events associated with the transition from the benign (adenoma) to the malignant (carcinoma) state. See Vogelstein et al., *New England Journal of Medicine*, 319:525 (1988), Fearon and Vogelstein, *Cell*, 61:759–767 (1990) and Baker et al. *Cancer Res*. 50:7717–22 (1990). More recently, comparative genomic hybridization has shown that specific patterns of chromosomal gains and losses take place during colorectal carcinogenesis (see, e.g. Schlegel, et al. *Cancer Research*. 55, 6002–6005 (1995); Ried, et al. *Genes, Chromosomes & Cancer* 15, 234–245 (1996); and Nakao et al., *Jpn. J. Surg*. 28, 567–569 (1998). These changes included overrepresentation (amplification) of large portion of chromosome 20 material.

Because carcinomas are often lethal, while the precursor adenomas are uniformly curable, the early detection of chromosomal changes associated with this transition are of considerable importance. The identification of regions of chromosomal abnormalities in other cancers is obviously great use in diagnosis, prognosis and treatment of these diseases. The present invention addresses these and other needs.

SUMMARY OF THE INVENTION

The present invention provides methods of screening for colon carcinoma cells in a sample. The methods comprise providing a nucleic acid sample from a premalignant lesion in colorectal tissue from a human patient and contacting the sample with a nucleic acid probe that selectively hybridizes to a chromosomal region on 20q. The formation of a hybridization complex is then detected and the presence or absence of increased copy number at 20q (usually 20q13.2) is determined.

The sample used can be, for instance, one suitable for in situ hybridization techniques, such as a metaphase spread or an interphase nucleus. Usually, the probe is labeled, e.g. with fluorescent label, which can be attached directly or indirectly to the probe. In some embodiments, a second probe that selectively hybridizes to a second chromosomal region is used as a reference. In these embodiments, the second probe is labeled with a fluorescent label distinguishable from the label on the probe that selectively hybridizes to a chromosomal region on 20q.

The sample can be derived from any premalignant colorectal tissue suspected of containing cancer cells. Often, the premalignant tissue is an ademomatous polyp or tissue showing high grade dysplasia.

In some embodiments the probe may comprise repetitive sequences. In this the methods may further comprise the step of blocking the hybridization capacity of repetitive sequences in the probe. This can be done by, for example, including unlabeled blocking nucleic acids with the labeled probe. The unlabeled blocking nucleic acids can be,f for example, Cot-1 DNA.

A number of hybridization formats can be used. In some formats, the probe is bound to a solid substrate as a member of an array of probes. In these embodiments, the probe is not labeled and the sample nucleic acids are labeled.

Definitions

To facilitate understanding of the invention, a number of terms are defined below.

The term "amplicon" as used herein refers to a region of genomic nucleic acid which, when present in altered copy number, is associated with cancer. For example, the invention provides nucleic acid sequences which, when present in aberrant copy number, are associated with colon cancer.

The term "20q13.2 amplicon" refers to a region on the q arm of human chromosome 20 at about band 13.2 that has been identified in cancer cells. This amplicon has been extensively analyzed (see, e.g., WO 98/02539) in breast cancer cells. A 1.5 megabase (Mb) wide amplified region within 20q13.2 was identified (Stokke (1995) *Genomics* 26: 134–137); Tanner (1994) *Cancer Res*. 54:4257–4260). Interphase FISH revealed low-level (>1.5x) and high level (>3x) 20q13.2 sequence amplification in 29% and 7% of breast cancers, respectively (Tanner (1995) *Clin. Cancer Res*. 1: 1455–1461). High level amplification was associated with an aggressive tumor phenotype (Tanner (1995) supra; Courjal (1996) *Br. J. Cancer* 74: 1984). Another study, using FISH to analyze 14 loci along chromosome 20q in 146 uncultured breast carcinomas, identified three independently amplified regions, including RMC20C001 region at 20q13.2 (highly amplified in 9.6% of the cases), PTPN1 region 3 Mb proximal (6.2%), and AIB3 region at 20q11 (6.2%) (Tanner (1996) Cancer Res. 56:3441–3445).

An "animal" refers to a member of the kingdom Animalia, characterized by multicellularity, the possession of a nervous system, voluntary movement, internal digestion, etc. An "animal" can be a human or other mammal. Preferred animals include humans, non-human primates, and other mammals. Thus, it will be recognized that the methods of this invention contemplate veterinary applications as well as medical applications directed to humans.

A "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. Cancers include, but are not limited to breast cancer, lung cancer, bronchus cancer, colorectal cancer, prostate cancer, pancreas cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testis cancer, biliary tract cancer, small bowel or appendix cancer, salivary gland cancer, thyroid gland cancer, adrenal gland cancer, osteosarcoma, chondrosarcoma, and the like.

The phrase "detecting a cancer" refers to the ascertainment of the presence or absence of cancer in an animal, in this case, colorectal premalignant tissue. "Detecting a cancer" can also refer to obtaining indirect evidence regarding the likelihood of the presence of cancerous cells in the animal or to the likelihood or predilection to development of a cancer. Detecting a cancer can be accomplished using the methods of this invention alone, or in combination with other methods or in light of other information regarding the state of health of the animal.

The terms "hybridizing specifically to" and "specific hybridization" and "tselectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt 2, "Overview of principles of hybridization and the strategy of nucleic acid probe assays,"* Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1–3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

The term "labeled with a detectable composition", as used herein, refers to a nucleic acid attached to a detectable composition, i.e., a label. The detection can be by, e.g., spectroscopic, photochemical, biochemical, immunochemical, physical or chemical means. For example, useful labels include $^{32}P$, $^{35}S$, $^{3}H$, $^{14}C$, $^{125}I$, $^{131}I$; fluorescent dyes (e.g., FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g. Dynabeads™), biotin, dioxigenin, or haptens and proteins for which antisera or monoclonal antibodies are available. The label can be directly incorporated into the nucleic acid, peptide or other target compound to be detected, or it can be attached to a probe or antibody that hybridizes or binds to the target. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). Label can be attached by spacer arms of various lengths to reduce potential steric hindrance or impact on other useful or desired properties. See, e.g., Mansfield (1995) *Mol Cell Probes* 9: 145–156.

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189–197. Other synthetic backbones encompasses by the term include methylphosphonate linkages or alternating methylphosphonate and phosphodiester linkages (Strauss-Soukup (1997) *Biochemistry* 36: 8692–8698), and benzylphosphonate linkages (Samstag (1996) *Antisense Nucleic Acid Drug Dev* 6:153–156). The term nucleic acid is used interchangeably with gene, cDNA, mRNA, oligonucleotide primer, probe and amplification product.

The term a "nucleic acid array" as used herein is a plurality of target elements, each target element comprising one or more nucleic acid molecules (probes) immobilized on one or more solid surfaces to which sample nucleic acids can be hybridized. The nucleic acids of a target element can contain sequence(s) from specific genes or clones, e.g. from the regions identified here. Other target elements will contain, for instance, reference sequences. Target elements of various dimensions can be used in the arrays of the invention. Generally, smaller, target elements are preferred. Typically, a target element will be less than about 1 cm in diameter. Generally element sizes are from 1 $\mu$m to about 3 mm, preferably between about 5 $\mu$m and about 1 mm. The target elements of the arrays may be arranged on the solid surface at different densities. The target element densities will depend upon a number of factors, such as the nature of the label, the solid support, and the like. One of skill will recognize that each target element may comprise a mixture of nucleic acids of different lengths and sequences. Thus, for example, a target element may contain more than one copy of a cloned piece of DNA, and each copy may be broken into fragments of different lengths. The length and complexity of the nucleic acid fixed onto the target element is not critical to the invention. One of skill can adjust these factors to provide optimum hybridization and signal production for a given hybridization procedure, and to provide the required resolution among different genes or genomic locations. In various embodiments, target element sequences will have a complexity between about 1 kb and about 1 Mb, between about 10 kb to about 500 kb, between about 200 to about 500 kb, and from about 50 kb to about 150 kb.

The terms "nucleic acid sample" or "sample of human nucleic acid" as used herein refers to a sample comprising human DNA or RNA in a form suitable for detection by hybridization or amplification. Typically, it will be prepared from a premalignant tissue sample from a patient who has or is suspected of having colorectal cancer. The sample will most usually be prepared from polyp tissue.

In many instances, the nucleic acid sample will be a tissue or cell sample prepared for standard in situ hybridization methods described below. The sample is prepared such that individual chromosomes remain substantially intact and typically comprises metaphase spreads or interphase nuclei prepared according to standard techniques. Alternatively, the nucleic acid may be isolated, cloned or amplified. It may be, e.g., genomic DNA, mRNA, or cDNA from a particular chromosome, or selected sequences (e.g. particular promoters, genes, amplification or restriction fragments, cDNA, etc.) within particular amplicons or deletions disclosed here.

The nucleic acid sample is extracted from colon adenoma cells or tissues. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves from cell cultures, cells from tissue culture and other media in which it may be desirable to detect chromosomal abnormalities or determine amplicon copy number. In some cases, the nucleic acids may be amplified using standard techniques such as PCR, prior to the hybridization. The sample may be isolated nucleic acids immobilized on a solid.

A "premalignant lesion", as used herein refers to benign adenomatous colon tissue (e.g. a polyp) that has the potential of malignant transformation. Polyps are exceedingly common. Cytologically adenomas show varying degrees of dysplasia ranging form mild to severe. There is virtually no distinction between severe dysplasia and carcinoma in situ, except that, dysplastic lesions, by definition, show no evidence of visible invasion. Polyps are generally removed by colonoscopic polypectomy.

The term "probe" or a "nucleic acid probe", as used herein, is defined to be a collection of one or more nucleic acid fragments whose hybridization to a sample can be detected. The probe may be unlabeled or labeled as described below so that its binding to the target or sample can be detected. The probe is produced from a source of nucleic acids from one or more particular (preselected) portions of the genome, e.g., one or more clones, an isolated whole chromosome or chromosome fragment, or a collection of polymerase chain reaction (PCR) amplification products. The probes of the present invention are produced from nucleic acids found in the regions described herein. The probe or genomic nucleic acid sample may be processed in some manner, e.g., by blocking or removal of repetitive nucleic acids or enrichment with unique nucleic acids. The word "sample" may be used herein to refer not only to detected nucleic acids, but to the detectable nucleic acids in the form in which they are applied to the target, e.g., with the blocking nucleic acids, etc. The blocking nucleic acid may also be referred to separately. What "probe" refers to specifically is clear from the context in which the word is used. The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) *Science* 767–773; Johnston (1998) *Curr. Biol.* 8: R171–R174; Schummer (1997) *Biotechniques* 23: 1087–1092; Kern (1997) *Biotechniques* 23: 120–124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

"Providing a nucleic acid sample" means to obtain a biological sample for use in the methods described in this invention. Most often, this will be done by removing a sample of cells from an animal, but can also be accomplished by using previously isolated cells (e.g. isolated by another person), or by performing the methods of the invention in vivo.

"Tissue biopsy" refers to the removal of a biological sample for diagnostic analysis. In a patient with cancer, tissue may be removed from a tumor, allowing the analysis of cells within the tumor.

DESCRIPTION OF THE SPECIFIC EMBODIMENTS

The present invention is based, at least in part, on the identification of particular chromosomal abnormalities associated with the transition from an adenoma to carcinoma in colorectal cancer. Colorectal cancer is the second leading cause of cancer related deaths in the United States and other Western countries. Unlike lung cancer, for example, in which smoking has been identified as the prime etiologic factor responsible for the disease, the principle mechanisms underlying colorectal cancer are complex and incompletely understood.

The development of colon adenocarcinoma, like many other cancers, is a multi-step progression to malignancy. The concept of multi-step carcinogenesis means that cancers evolve slowly over time during which the surrounding tissue becomes increasingly abnormal. The features of the early, intermediate and advanced stages of multi-step malignant progression have been described using microscopy. The first stage of neoplastic progression is an increased number of relatively normal appearing cells, the hyperplastic stage. There are several stages of hyperplasia in which the cells progressively accumulate and begin to develop an abnormal appearance, which is the emergence of the dysplastic phase. Dysplastic cells resemble immature epithelial cells, and during this phase of neoplastic progression, an increasing percentage of the epithelium is composed of these immature cells. Eventually, invasive cancers develop in tissue severely affected by dysplasia.

The critical issue in treatment of benign polyps is to decide whether or not to proceed with colectomy in the case in which the removed polyp contains malignant foci. Generally, if the carcinomatous tissue is restricted superficially and does not penetrate the muscolaris mucosa the carcinoma (in situ carcinoma or intramucosal carcinoma) no further surgical treatment is performed, while if the malignant foci has penetrated into the muscolaris mucosa the lesion is considered invasive and therefore colonic resection may be carried out. However the distinction between intra-mucosal carcinomas/high dysplastic lesion and invasive carcinoma may sometime difficult to achieve even by an experienced pathologist especially in the case of sessile or friable lesions or when the lesion have been morphologically altered in resection.

The present invention provides alternative criteria by which this transition can be determined. As demonstrated below, amplification of the human chromosomal region at 20q (particularly at 20q13.2), is a frequent event in colon adenocarcinomas, occurring in approximately 80% of the cases. This molecular alteration is, however, a vary rare event in premalignant lesions, i.e. adenomas (polyps). In addition, intermediary diagnostic stages in the colon cancer natural history, i.e. high grade dysplasia and intramucosal carcinoma, display increased copy number of this chromosomal region in approximately 50% of the cases. These intermediary stages are thought to be the precursors of adenocarcinoma. Thus, detection of the 20q13.2 amplicon or other regions an 20q in colon tissue polyps can be used to the diagnose the stage and therefore with the gravity of the lesion.

The assays of the invention can also be used for prognosis of disease. For instance, the presence of the amplicon in high grade dysplasia/intramucosal carcinoma lesions can be used to predict whether the lesions will display hystopathological and cytopathological features similar to the invasive colon carcinomas. Thus, the assays of the invention can be an import tool in decision making for both surgery and therapy of those patients that have high grade preadenomatous lesions. Similarly, the presence of 20q13.2 amplicon in colon adenocarcinomas can be correlated with poor clinical outcome.

Detection of Copy Number

In the preferred embodiment, the presence of colon carcinoma cells is evaluated by a determination of copy number of regions on 20q identified here. Methods of evaluating the copy number of a particular gene or chromosomal region are well known to those of skill in the art.

Hybridization-based Assays

Preferred hybridization-based assays include, but are not limited to, traditional "direct probe" methods such as Southern Blots or In Situ Hybridization (e.g., FISH), and "comparative probe" methods such as Comparative Genomic Hybridization (CGH). The methods can be used in a wide variety of formats including, but not limited to substrate—(e.g. membrane or glass) bound methods or array-based approaches as described below.

In situ hybridization assays are well known (e.g., Angerer (1987) *Meth. Enzymol* 152: 649). Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. The preferred size range is from about 200 bp to about 1000 bases, more preferably between about 400 to about 800 bp for double stranded, nick translated nucleic acids.

In some applications it is necessary to block the hybridization capacity of repetitive sequences. Thus, in some embodiments, human genomic DNA or Cot-1 DNA is used to block non- specific hybridization.

In Comparative Genomic Hybridization methods a first collection of (sample) nucleic acids (e.g. from a possible tumor) is labeled with a first label, while a second collection of (control) nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number.

Hybridization protocols suitable for use with the methods of the invention are described, e.g., in Albertson (1984) *EMBO J*. 3: 1227–1234; Pinkel (1988) *Proc. Natl. Acad. Sci. USA* 85: 9138–9142; EPO Pub. No. 430,402; *Methods in Molecular Biology*, Vol. 33: *In Situ Hybridization Protocols*, Choo, ed., Humana Press, Totowa, N.J. (1994), etc. In one particularly preferred embodiment, the hybridization protocol of Pinkel et al. (1998) Nature Genetics 20: 207–211 or of Kallioniemi (1992) *Proc. Natl Acad Sci USA* 89:5321–5325 (1992) is used.

The methods of this invention are particularly well suited to array-based hybridization formats. For a description of one preferred array-based hybridization system see Pinkel et al. (1998) *Nature Genetics*, 20: 207–211.

Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) Genome Res. 7: 606–614; Jackson (1996) *Nature Biotechnology* 14:1685; Chee (1995) *Science* 274: 610; WO 96/17958.

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. : 5,807,522). This patent describes the use of an automated systems that taps a microcapillary against a surface to deposit a small volume of a biological sample. The process is repeated to generate high density arrays. Arrays can also be produced using oligonucleotide synthesis technology. Thus, for example, U.S. Pat. No. 5,143,854 and PCT patent publication Nos. WO 90/15070 and 92/10092 teach the use of light-directed combinatorial synthesis of high density oligonucleotide arrays.

In another embodiment the array, particularly a spotted array, can include genomic DNA, e.g. overlapping clones that provide a high resolution scan of the amplicon corresponding to the region of interest. Amplicon nucleic acid can be obtained from, e.g., MACs, YACs, BACs, PACs, Pls, cosmids, plasmids, inter-Alu PCR products of genomic clones, restriction digests of genomic clone, cDNA clones, amplification (e.g., PCR) products, and the like.

In various embodiments, the array nucleic acids are derived from previously mapped libraries of clones spanning or including the target sequences of the invention, as well as clones from other areas of the genome, as described below. The arrays can be hybridized with a single population of sample nucleic acid or can be used with two differentially labeled collections (as with an test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g. Denhardt's solution) can be employed to avoid non-specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

For example, methods for immobilizing nucleic acids by introduction of various functional groups to the molecules is known (see, e.g., Bischoff (1987) *Anal. Biochem.*, 164: 336–344; Kremsky (1987) *Nucl. Acids Res*. 15: 2891–2910). Modified nucleotides can be placed on the target using PCR primers containing the modified nucleotide, or by enzymatic end labeling with modified nucleotides. Use of glass or membrane supports (e.g., nitrocellulose, nylon, polypropylene) for the nucleic acid arrays of the invention is advantageous because of well developed technology employing manual and robotic methods of arraying targets at relatively high element densities. Such membranes are generally available and protocols and equipment for hybridization to membranes is well known.

Target elements of various sizes, ranging from 1 mm diameter down to 1 $\mu$m can be used. Smaller target elements containing low amounts of concentrated, fixed probe DNA are used for high complexity comparative hybridizations since the total amount of sample available for binding to each target element will be limited. Thus it is advantageous to have small array target elements that contain a small amount of concentrated probe DNA so that the signal that is obtained is highly localized and bright. Such small array target elements are typically used in arrays with densities greater than $10^4/cm^2$. Relatively simple approaches capable of quantitative fluorescent imaging of 1 $cm^2$ areas have been described that permit acquisition of data from a large number of target elements in a single image (see, e.g., Wittrup (1994) Cytometry 16:206–213).

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques (described above). Nucleic acids can be conveniently coupled to glass using commercially available reagents. For instance, materials for preparation of silanized glass with a number of functional groups are commercially available or can be prepared using standard techniques (see, e.g., Gait (1984) Oligonucleotide Synthesis: A Practical Approach, IRL Press, Wash., D.C.). Quartz cover slips, which have at least 10-fold lower autofluorescence than glass, can also be silanized.

Alternatively, probes can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith (1992) *Science* 258: 1122–1126). Biotin or digoxigenin end-labeled nucleic acids can be prepared according to standard techniques. Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

In one particularly preferred embodiment, probe nucleic acid is spotted onto a surface (e.g., a glass or quartz surface). The nucleic acid is dissolved in a mixture of dimethylsulfoxide (DMSO) and nitrocellulose and spotted onto aminosilane coated glass slides. Small capillaries tubes can be used to "spot" the probe mixture.

A variety of other nucleic acid hybridization formats are known to those skilled in the art. For example, common formats include sandwich assays and competition or displacement assays. Hybridization techniques are generally described in Hames and Higgins (1985) *Nucleic Acid Hybridization, A Practical Approach*, IRL Press; Gall and Pardue (1969) *Proc. Natl. Acad. Sci. USA* 63: 378–383; and John et al. (1969) *Nature* 223: 582–587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE-T at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.1 to about 0.5 mg/ml DNA (e.g., cot-1 DNA). The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology*, Vol. 24: *Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background membranes can be used (see, e.g., Chu (1992) *Electrophoresis* 13:105–114). The sensitivity for detection of spots ("target elements") of various diameters on the candidate membranes can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., membranes, glass, fused silica) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

Labeling and Detection of Nucleic Acids.

In a preferred embodiment, the hybridized nucleic acids are detected by detecting one or more labels attached to the sample or probe nucleic acids. The labels may be incorporated by any of a number of means well known to those of skill in the art. Means of attaching labels to nucleic acids include, for example nick translation or endlabeling (e.g. with a labeled RNA) by kinasing of the nucleic acid and subsequent attachment (ligation) of a nucleic acid linker joining the sample nucleic acid to a label (e.g., a fluorophore). A wide variety of linkers for the attachment of labels to nucleic acids are also known. In addition, intercalating dyes and fluorescent nucleotides can also be used.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752;3, 939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence. Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science*, 281: 2013–2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016–2018).

Amplification-based Assays.

In another embodiment, amplification-based assays can be used to measure copy number. In such amplification-based assays, the nucleic acid sequences act as a template in an amplification reaction (e.g. Polymerase Chain Reaction (PCR). In a quantitative amplification, the amount of amplification product will be proportional to the amount of template in the original sample. Comparison to appropriate (e.g. healthy tissue) controls provides a measure of the copy number of the desired target nucleic acid sequence. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.).

Other suitable amplification methods include, but are not limited to ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), and self-sustained sequence replication (Guatelli et al. (1990) *Proc. Nat. Acad. Sci. USA* 87: 1874).

Detection of Gene Expression

As indicated below, a number of oncogenes are found in the regions of amplification disclosed here. Thus, oncogene activity can be detected by, for instance, measuring levels of the gene transcript (e.g. mRNA), or by measuring the quantity of translated protein.

Detection of Gene Transcripts.

Methods of detecting and/or quantifying t gene transcripts using nucleic acid hybridization techniques are known to those of skill in the art (see Sambrook et al. supra). For example, a Northern transfer may be used for the detection of the desired mRNA directly. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target mRNA.

In another preferred embodiment, the gene transcript can be measured using amplification (e.g. PCR) based methods as described above for directly assessing copy number of the target sequences.

Detection of Expressed Protein

The "activity" of the target onocgene can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

Kits for Use in Diagnostic and/or Prognostic Applications.

For use in diagnostic, research ,and therapeutic applications suggested above, kits are also provided by the invention. In the diagnostic and research applications such kits may include any or all of the following: assay reagents, buffers, nucleic acids for detecting the target sequesences and other hybridization probes and/or primers. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

This examples provides a detailed protocol using FISH analysis to detect the 20q13.2 amplicon in colon tissue sections. The method was tested in 140 archival tissue specimens.

Materials and Methods

Tissue Specimens and Slide Preparation

Four micron sections were cut from archival tissue which had been fixed in buffered formalin and embedded in paraffin and placed on aminoalkylsilane-treated slides. Silanization of the slides was for 5 min in a 2% 3-aminopropyltriethoxysilane solution (Sigma Chemical Co., St. Louis, Mo.) in acetone, followed by successive washes in acetone and distilled water. Slide mounted tissue sections were then baked overnight at 65° C. and deparaffinized in xylenes for 10 min.×3, followed by immersion in ethanol. Air dried sections were subsequently treated in 1N. Sodium thiocyanate for 20 min. at 80° C., washed 3× in 2×SSC and then treated in as solution of proteinase K in 2×SSC (250 μg./ml.) for 20 min at 37 C. Tissue section were then washed in 2×SSC as above and dehydrated in 70% EtOH and then in acetone for 2 min each.

Probe

A probe spanning approximately 200 kb of the chromosomal region containing the ZNF217 gene was utilized to detect the presence or absence of 20q13.2 amplification. The probe spans from about D20S854 to about D2020S876 (see, Collins et al. *Proc. Natl. Acad. Sci. U.S.A.* 95:8703–8708 (1998) for a description of the 20q13.2 amplicon and ZNF217 gene). The probe was directly labeled with the fluorophore SpectrumOrange™ (Vysis, Inc., Downers Grove, Ill.).

In Situ Hybridization

Slide mounted tissue sections were denatured in 70% formamide/2×SSC, pH7.0 at 85° C. for 10 min and then immersed in 100% EtOH al −20° C. Before applying the hybridization mixture onto tissue sections, slides were air-dried and warmed to 45° C. The hybridization mixture contained 50% formamide/10% dextran sulfate/2×SSC. Concentration of probe was 10 ng/ml and hybridization of repetitive DNA sequences was suppressed by inclusion of 0.5 μg of human Cot-1 DNA (Gibco BRL, Grand Island, N.Y.). The hybridization mixture was denatured for 10 min at 100° C. and allowed to reanneal for 20–30 min at 37° C. Hybridization was carried out overnight at 42° C. (direct-labeled probe) under a coverslip in a moist chamber. Washes were performed respectively at 45° C. as follows: twice in 50% formamide/2×SSC for 15 min each, twice in 0.1% Triton X-100/2×SSC for 10 min each. Tissue sections were counterstained using 0.15 mM 4,6 diamidino-2-phenylindo (DAPI) (Sigma Chemical Co., St. Louis, Mo.) in 2×SSC for 5 min, destained in 2×SSC for 5 min, dehydrated in 100% EtOH, air dried and mounted in antifade solution (Vector Laboratories, Inc., Burlingame, Calif.).

Fluorescence Microscopy

A Zeiss epifluorescence microscope equipped with a 100 watt mercury-arc lamp and high numerical aperture Neofluor objectives was used with the following single-band pass fitter combinations: DAPI 02 (Carl Zeiss, Inc., Thornwood, N.Y.), High Q FITC (Chroma Technology Corp., Brattleboro, Vt.), FITC 09 (Carl Zeiss, Inc., Thornwood, N.Y.) and a specially designed fitter combination optimized for SpectrumOrange detection (Vysis, Inc., Downers Grove, Ill.).

Results

Using the techniques described above, it was found that more than 2/3 of colon cancers contain amplification at 20q13.2. The finding is especially useful in diagnostics. The only methods presently available for the diagnosis of colon lesions is by direct examination by a pathologist. The 20q13.2 amplicon can easily be tested for using this approach and provides clear-cut confirmation of diagnosis. Second, the diagnosis of intramucosal carcinomas (IMCa) is particularly difficult and somewhat subjective depending heavily on the pathologist. Determination of a diagnosis of IMCa could make the difference between more or less aggressive therapies.

What is claimed is:

1. A method of screening for colon carcinoma precursor cells in a sample by determining the presence of increased copy number of chromosome 20q, the method comprising:

providing a nucleic acid sample from a premalignant lesion in colorectal tissue from a human patient;

contacting the sample with a nucleic acid probe that selectively hybridizes to a chromosomal region on 20q; and detecting the formation of a hybridization complex, whereby the presence of increased copy number on 20q indicates the presence of colon cancer precursor cells.

2. The method of claim 1, wherein the chromosomal region is 20q13.2.

3. The method of claim 2, wherein the probe selectively hybridizes to ZNF217.

4. The method of claim 1, wherein the nucleic acid sample is a metaphase spread or an interphase nucleus.

5. The method of claim 1, wherein the probe is labeled.

6. The method of claim 4, wherein the label is a fluorescent label.

7. The method of claim 5, wherein the label is a direct label.

8. The method of claim 5, further comprising contacting the sample with a second probe that selectively hybridizes to a second chromosomal region.

9. The method of claim 7, wherein the second probe is labeled with a fluorescent label distinguishable from the label on the probe that selectively hybridizes to a chromosomal region on 20q.

10. The method of claim 1, wherein the premalignant tissue is an adenomatous polyp.

11. The method of claim 1, wherein the premalignant tissue shows high grade dysplasia.

12. The method of claim 1, further comprising the step of blocking the hybridization capacity of repetitive sequences in the probe.

13. The method of claim 12, wherein unlabeled blocking nucleic acids comprising repetitive sequences are contacted with the sample.

14. The method of claim 12, wherein the unlabeled blocking nucleic acids are Cot-1 DNA.

15. The method of claim 1, wherein probe is bound to a solid substrate.

16. The method of claim 15, wherein the probe is a member of an array.

17. The method of claim 1, wherein the nucleic acid sample is from archived material.

18. The method of claim 1, further comprising selecting a therapeutic treatment based on the determined presence of increased copy number at 20q.

19. A method of screening for colon carcinoma precursor cells in a sample by determining the presence of increased copy number of chromosome 20q13.2, the method comprising:

providing a nucleic acid sample comprising a metaphase spread or an interphase nucleus from a premalignant lesion in colorectal tissue from a human patient;

contacting the sample with a fluorescently labeled nucleic acid probe that selectively hybridizes to a chromosomal region at 20q13.2 and detecting the formation of a hybridization complex, whereby the presence of increased copy number at 20q13.2 indicates the presence of colon carcinoma precursor cells.

20. The method of claim 19, further comprising contacting the sample with a second probe that selectively hybridizes to a second chromosomal region.

21. The method of claim 20, wherein the second chromosomal region is a centromere.

22. The method of claim 20, wherein the second probe is labeled with a fluorescent label distinguishable from the label on the probe that selectively hybridizes to a chromosomal region at 20q13.2.

23. The method of claim 19, wherein the premalignant tissue is an adenomatous polyp.

24. The method of claim 19, wherein the premalignant tissue shows high grade dysplasia.

25. The method of claim 19, wherein the probe selectively hybridizes to ZNF217.

* * * * *